(12) United States Patent
Hill

(10) Patent No.: US 7,640,782 B2
(45) Date of Patent: Jan. 5, 2010

(54) VAPORIZED HYDROGEN PEROXIDE PROBE CALIBRATION RIG

(75) Inventor: Aaron L. Hill, Erie, PA (US)

(73) Assignee: American Sterilizer Company, Mentor, OH (US)

(*) Notice: Subject to any disclaimer, the term of this patent is extended or adjusted under 35 U.S.C. 154(b) by 306 days.

(21) Appl. No.: 11/740,973

(22) Filed: Apr. 27, 2007

(65) Prior Publication Data

US 2008/0264140 A1 Oct. 30, 2008

(51) Int. Cl.
G01N 21/00 (2006.01)
(52) U.S. Cl. ........................................... 73/1.02
(58) Field of Classification Search ................. 73/1.02, 73/23.2
See application file for complete search history.

(56) References Cited

U.S. PATENT DOCUMENTS

| | | | |
|---|---|---|---|
| 4,007,096 A | 2/1977 | Jasinski et al. | 204/1 |
| 4,045,721 A | 8/1977 | Swain | 320/43 |
| 4,843,867 A | 7/1989 | Cummings | 73/23 |
| 4,952,370 A | 8/1990 | Cummings et al. | 422/28 |
| 4,956,145 A | 9/1990 | Cummings et al. | 422/28 |
| 5,122,344 A | 6/1992 | Schmoegner | 422/111 |
| 5,173,258 A | 12/1992 | Childers | 422/27 |
| 5,492,672 A | 2/1996 | Childers et al. | 422/28 |
| 5,600,142 A | 2/1997 | Van Den Berg et al. | 250/339.13 |
| 5,847,392 A | 12/1998 | Van Den Berg et al. | 250/339.09 |
| 5,872,359 A * | 2/1999 | Stewart et al. | 250/339.12 |
| 5,876,664 A | 3/1999 | Childers et al. | 422/28 |
| 5,906,794 A | 5/1999 | Childers | 422/28 |
| 5,944,048 A | 8/1999 | Bump et al. | 137/487.5 |
| 6,581,435 B2 * | 6/2003 | Wang et al. | 73/1.02 |
| 6,612,149 B2 | 9/2003 | Wang et al. | 73/1.02 |
| 6,742,378 B2 | 6/2004 | Wang et al. | 73/1.02 |
| 6,953,549 B2 | 10/2005 | Hill et al. | 422/30 |
| 7,157,046 B2 | 1/2007 | McVey et al. | 422/28 |
| 7,186,374 B2 | 3/2007 | Zelina et al. | 422/28 |
| 7,238,330 B2 | 7/2007 | Hill et al. | 422/292 |
| 2002/0114727 A1 | 8/2002 | McVey et al. | 422/4 |
| 2005/0252274 A1 | 11/2005 | Centanni | 73/23.2 |
| 2006/0088441 A1 | 4/2006 | Hill | 422/30 |
| 2007/0098592 A1 | 5/2007 | Buczynski et al. | 422/3 |

OTHER PUBLICATIONS

Schumb et al., "Hydrogen Peroxide," American Chemical Society, Monograph Series, Reinhold Publishing Corporation, New York, NY, Chapman & Hall, Ltd., London, pp. 176-181.
U.S. Appl. No. 11/421,265, filed May 31, 2006, Buczynski, entitled: Decontamination System With Air Bypass.

(Continued)

*Primary Examiner*—Hezron Williams
*Assistant Examiner*—Alex Devito
(74) *Attorney, Agent, or Firm*—Kusner & Jaffe; Michael A. Centanni

(57) ABSTRACT

A method and apparatus for calibrating a sensor used to sense the concentration of vaporized hydrogen peroxide (VHP). A concentration of liquid hydrogen peroxide in an aqueous solution is determined and correlated with a corresponding concentration of vaporized hydrogen peroxide indicative of an "actual" vaporized hydrogen peroxide concentration. An error value is determined by comparing the "actual" vaporized hydrogen peroxide concentration to a "measured" vaporized hydrogen peroxide concentration, indicated by the sensor being calibrated. The error value is used to properly calibrate the sensor.

16 Claims, 2 Drawing Sheets

OTHER PUBLICATIONS

U.S. Appl. No. 11/463,608, filed Aug. 10, 2006, Hill, entitled: Modular Decontamination System.

U.S. Appl. No. 11/741,069, filed Apr. 27, 2007, Hill, entitled: Vaporized Hydrogen Peroxide Decontamination System With Concentration Adjustment Mode.

U.S. Appl. No. 11/741,299, filed Apr. 27, 2007, Hill, entitled: Hydrogen Peroxide Vaporizer.

U.S. Appl. No. 11/838,327, filed Aug. 14, 2007, Hill, entitled: Method and Apparatus for Decontaminating a Region Without Dehumidification.

* cited by examiner

VAPORIZED HYDROGEN PEROXIDE PROBE CALIBRATION RIG

FIELD OF THE INVENTION

The present invention relates generally to the art of sensor calibration, and more particularly to a method and apparatus for calibrating a sensor used to sense a concentration of a chemical.

BACKGROUND OF THE INVENTION

Sensors for sensing the concentration of a chemical agent are advantageous in a variety of industrial and medical applications. One such application is sensing a concentration of a gaseous or vaporous decontaminating agent (e.g., vaporized hydrogen peroxide) used for decontamination of medical instruments isolators, rooms, etc. Successful decontamination requires exposure to a predetermined concentration of a decontaminating agent over a predetermined period of time. Therefore, accurate measurement of the concentration of the decontaminating agent is advantageous to achieve adequate decontamination and efficient utilization of the decontaminating agent.

In order to insure accuracy, sensors used for measuring, i.e., sensing, the concentration of decontaminating agents are periodically calibrated. According to conventional calibration methods, a sensor for sensing the concentration of decontaminating agents is calibrated by exposing the sensor to a sample of the decontaminating agent at a known concentration. After the sensor is exposed to the sample, the sensor is adjusted to provide a signal that is indicative of the sensed concentration. In order to calibrate the sensor at different concentrations, the calibration method can be repeated using a series of samples having different known concentrations.

The foregoing calibration method is not well suited for calibrating sensors used to determine the concentration of unstable chemical agents such as vaporized hydrogen peroxide. In this regard, vaporized hydrogen peroxide will decompose into oxygen and water. Because vaporized hydrogen peroxide decomposes, a known, stable concentration of vaporized hydrogen peroxide may not be reliably prepared for use in calibrating a sensor using conventional methods. Accordingly, other methods of calibration have been developed to calibrate sensors used to determine the concentration of vaporized hydrogen peroxide, as will be described below.

Typical sensors used for determining the concentration of vaporized hydrogen peroxide include infrared (IR) sensors (e.g., near infrared (NIR) sensors) and electrochemical sensors.

A conventional IR sensor includes a source of infrared radiation ("IR source") and an infrared detector that are located a fixed distance apart. An optical filter is disposed either in front of the source of infrared radiation or the IR detector to screen out all radiation except for the wavelength that is absorbed by vaporized hydrogen peroxide. Vaporized hydrogen peroxide passes between the IR source and the IR detector.

The amount of IR radiation (provided by the IR source) that is absorbed by the vaporized hydrogen peroxide is proportional to the concentration of vaporized hydrogen peroxide. Accordingly, the IR sensor generates a signal that is indicative of the concentration of vaporized hydrogen peroxide based upon the proportion of IR radiation (provided by the IR source) that is received by the IR detector.

A conventional IR sensor is typically calibrated using an optical filter that is placed between the IR source and the IR detector. The optical filter blocks some of the IR radiation at the same wavelength absorbed by the vaporized hydrogen peroxide. In this regard, the optical filter simulates the presence of vaporized hydrogen peroxide at a known concentration. The IR sensor is adjusted such that it provides a signal indicative of the concentration of vaporized hydrogen peroxide simulated by the optical filter. One drawback to using an optical filter for calibration of IR sensors is that a range of different optical filters is required to calibrate an IR sensor over a range of concentrations.

A conventional electrochemical sensor reacts with vaporized hydrogen peroxide to produce an electrical signal proportional to the concentration of the vaporized hydrogen peroxide. A typical electrochemical sensor includes a first electrode and a second electrode that are connected by a resistor. A thin layer of electrolyte separates the first and second electrodes. The first electrode is formed of a material that is reactive with vaporized hydrogen peroxide.

Vaporized hydrogen peroxide that comes in contact with the reactive material of the first electrode participates in a chemical reaction that generates a current. The current flows between the two electrodes and is proportional to the concentration of vaporized hydrogen peroxide. Accordingly, the amount of current produced by the electrochemical sensor is indicative of the concentration of vaporized hydrogen peroxide.

As indicated above, vaporized hydrogen peroxide is an unstable vapor and will decompose over time. Therefore, a typical method for calibrating an electrochemical sensor for determining the concentration of vaporized hydrogen peroxide utilizes a surrogate vapor that does not decompose over time. The electrochemical sensor responds to the presence of the surrogate vapor in a known manner. In this regard, the response of the electrochemical sensor to a specific concentration of the surrogate vapor can be correlated to a response of the electrochemical sensor to the presence of a known concentration of vaporized hydrogen peroxide. A correlation method is required in order to use a surrogate vapor for calibrating an electrochemical sensor at a particular concentration of vaporized hydrogen peroxide. A drawback to using a surrogate vapor for calibration of an electrochemical sensor is that a single correlation method may be applicable only over a limited range of concentrations of vaporized hydrogen peroxide. As a result, multiple correlation methods may be required in order to calibrate a sensor across a range of vaporized hydrogen peroxide concentrations.

The present invention overcomes these and other problems by providing a method and apparatus for calibrating a sensor for sensing vaporized hydrogen peroxide by determining the concentration of hydrogen peroxide in an aqueous solution of hydrogen peroxide.

SUMMARY OF THE INVENTION

In accordance with the present invention, there is provided an apparatus for calibrating a concentration sensor for sensing concentration of vaporized hydrogen peroxide, said apparatus comprising: (a) an enclosure defining a chamber; (b) a first temperature sensor for generating a first signal indicative of the temperature within the chamber; (c) a vessel defining a cavity, said vessel including isolation means movable between a closed position for isolating the cavity from the chamber and an open position wherein the cavity is in fluid communication with the chamber; (d) first supply means for supplying an aqueous solution of hydrogen peroxide to the cavity; (e) a first concentration sensor for generating a second signal indicative of a concentration of liquid hydrogen peroxide within the cavity; (f) a controller storing data for correlating a concentration of liquid hydrogen peroxide to a concentration of vaporized hydrogen peroxide at a predetermined temperature, said vaporized hydrogen peroxide being derived from said aqueous solution of hydrogen peroxide. The controller includes: means for receiving the first signal generated by the first temperature sensor indicative of the temperature within the chamber and the second signal generated by the first concentration sensor indicative of the concentration of liquid hydrogen peroxide within the cavity; means for moving said isolation means from the closed position to the open position, thereby releasing vaporized hydrogen peroxide into said chamber; means for receiving a third signal generated by a second concentration sensor located within said chamber, said third signal indicative of a measured vaporized hydrogen peroxide concentration inside said chamber; means for determining an actual concentration of vaporized hydrogen peroxide inside said chamber using said first signal, said second signal and said stored data; means for comparing said measured concentration to said actual concentration to determine an error value; and means for calibrating said second concentration sensor in accordance with the determined error value.

In accordance with another aspect of the present invention, there is provided a method for calibrating a concentration sensor for sensing concentration of vaporized hydrogen peroxide, said method comprising the steps of: (a) filling a cavity defined by an enclosed vessel with an aqueous solution of liquid hydrogen peroxide, said cavity isolated by isolation means from a chamber defined by an enclosure; (b) storing data in a controller, said data correlating a concentration of liquid hydrogen peroxide at a predetermined temperature to a concentration of vaporized hydrogen peroxide; (c) locating a concentration sensor to be calibrated within said chamber, said concentration sensor generating a signal indicative of a measured concentration of vaporized hydrogen peroxide within said chamber; (d) moving said isolation means to put said cavity in fluid communication with said chamber, thereby releasing vaporized hydrogen peroxide into said chamber; (e) determining a concentration of the liquid hydrogen peroxide within said cavity; (f) determining a temperature within said cavity; (g) determining an actual concentration of vaporized hydrogen peroxide inside said chamber using said stored data, the temperature within said cavity, and the concentration of liquid hydrogen peroxide within said cavity; (h) comparing the measured concentration to the actual concentration to determine an error value; and (i) calibrating said concentration sensor located within said chamber in accordance with the determined error value.

According to still another aspect of the present invention, there is provided an apparatus for calibrating a concentration sensor for sensing concentration of vaporized hydrogen peroxide, said apparatus comprising: an enclosure; an open vessel located within the enclosure; a first temperature sensor providing a first signal indicative of the temperature within the enclosure; and a densitometer. The densitometer includes: a tube for holding a column of fluid having a height h, a pressure transducer for providing a pressure value for the column of a fluid having a height h, and a temperature sensor for sensing the temperature of the fluid in the tube. The apparatus further comprises a reservoir for providing a supply of an aqueous solution of hydrogen peroxide, said reservoir in fluid communication with the open vessel and the densitometer; and a controller for controlling operation of the apparatus. The controller comprises: means for determining the concentration of liquid hydrogen peroxide in the aqueous solution of hydrogen peroxide using the densitometer, means for storing data for correlating a concentration of liquid hydrogen peroxide to a concentration of vaporized hydrogen peroxide at a given temperature, said vaporized hydrogen peroxide being derived from said aqueous solution of hydrogen peroxide, means for activating a pump to transfer the aqueous solution of hydrogen peroxide from the reservoir to the open vessel, means for receiving a first signal generated by the first temperature sensor indicative of the temperature within the chamber and the second signal generated by the first concentration sensor indicative of the concentration of liquid hydrogen peroxide within the cavity, means for determining an actual concentration of vaporized hydrogen peroxide inside said enclosure by using the first signal indicative of the temperature within the enclosure and the stored data, means for determining an actual concentration of vaporized hydrogen peroxide inside said chamber by accessing said data according to the temperature and liquid hydrogen peroxide concentration respectively indicated by said first and second signals, means for receiving a second signal generated by a concentration sensor located within the enclosure, said second signal indicative of a measured concentration of vaporized hydrogen peroxide inside the enclosure, means for comparing the measured concentration with the actual concentration to determine an error value, and means for calibrating the concentration sensor located within the enclosure in accordance with the determined error value.

According to yet another aspect of the present invention, there is provided a method for calibrating a concentration sensor for sensing concentration of vaporized hydrogen peroxide, said method comprising the steps of: (a) storing data in a controller, said data correlating a concentration of liquid hydrogen peroxide at a predetermined temperature to a concentration of vaporized hydrogen peroxide; (b) locating a concentration sensor to be calibrated within an enclosure, said concentration sensor generating a signal indicative of a measured concentration of vaporized hydrogen peroxide within said enclosure; (c) determining density of an aqueous solution of liquid hydrogen peroxide; (d) determining a concentration of the liquid hydrogen peroxide using the determined density of the liquid hydrogen peroxide; (e) filling an open vessel within the enclosure with the aqueous solution of liquid hydrogen peroxide; (f) determining a temperature within the enclosure; (g) determining an actual concentration of vaporized hydrogen peroxide inside said enclosure using said stored data, the temperature within the enclosure and the concentration of liquid hydrogen peroxide; (h) comparing the measured concentration to the actual concentration to determine an error value; and (i) calibrating the concentration sensor located within the enclosure in accordance with the determined error value.

An advantage of the present invention is that it provides an apparatus for accurately calibrating a sensor used to sense a concentration of vaporized hydrogen peroxide.

Another advantage of the present invention is an apparatus as defined above that uses a liquid multi-component solution.

Still another of the present invention is an apparatus as defined above that uses an aqueous solution of hydrogen peroxide.

Yet another advantage of the present invention is an apparatus as defined above that can be used to calibrate multiple sensors during a calibration procedure.

BRIEF DESCRIPTION OF THE DRAWING

The invention may take physical form in certain parts and arrangement of parts, an embodiment of which will be described in detail in the specification and illustrated in the accompanying drawing which forms a part hereof, and wherein.

DETAILED DESCRIPTION OF THE INVENTION

Figure 1:
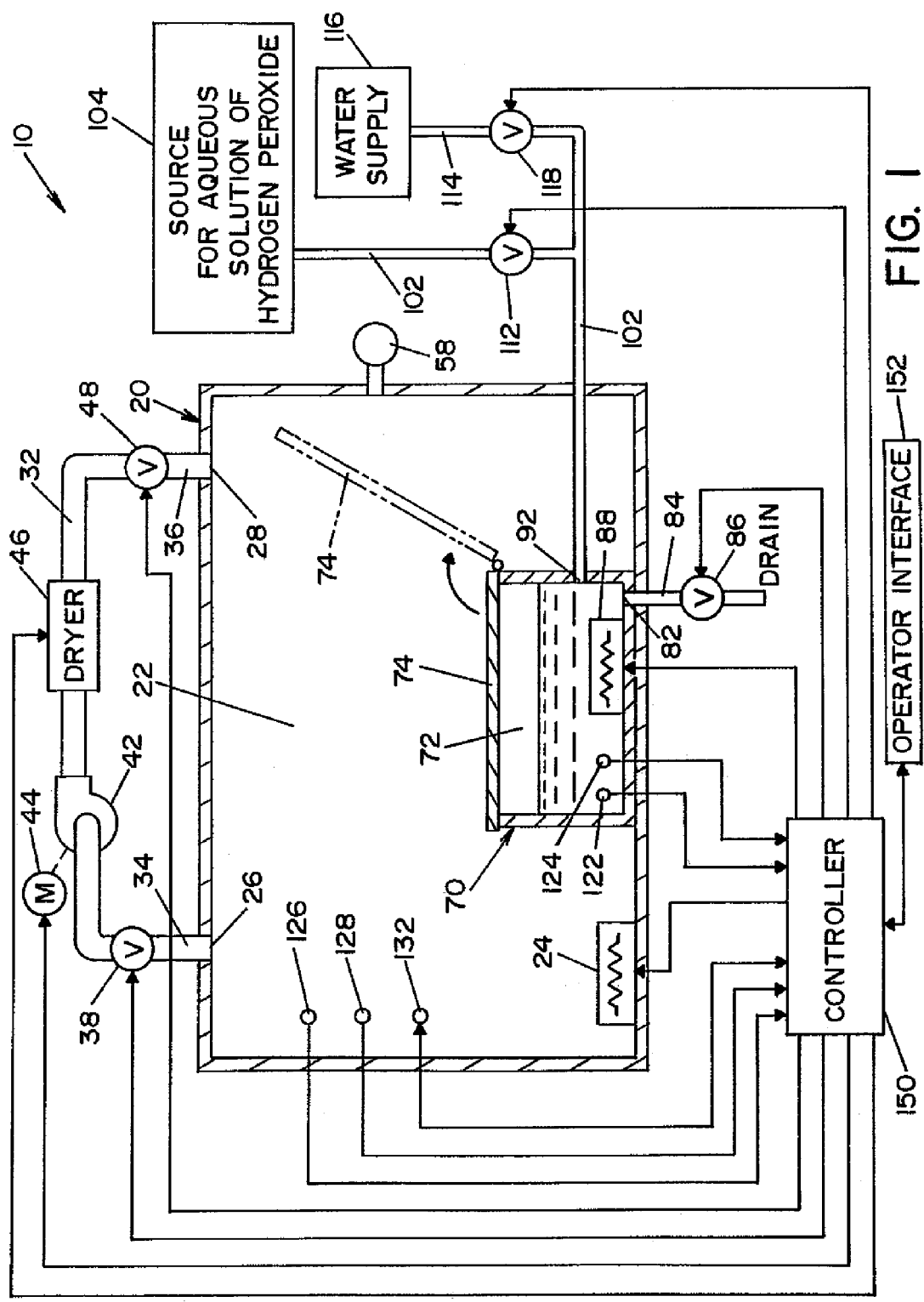
FIG. 1 is a schematic view of a first embodiment of an apparatus for calibrating a sensor used to sense the concentration of vaporized hydrogen peroxide.

Referring now to the drawings wherein the showings are for the purpose of illustrating an embodiment of the invention only, and not for the purpose of limiting same, FIG. 1 shows a calibration apparatus 10, according to a first embodiment, for calibrating a sensor used to determine the concentration of vaporized hydrogen peroxide.

Calibration apparatus 10 includes a housing 20 that defines a chamber 22 having a fixed volume. Housing 20 has an outlet port 26 and an inlet port 28 defined therein. A recirculation conduit 32 has a first end 34 that is fluidly connected to outlet port 26 and a second end 36 that is fluidly connected to inlet port 28. A blower 42 is disposed in recirculation conduit 32 between first end 34 and second end 36. A motor 44 is connected to blower 42 and is operable to drive blower 42 to recirculate the atmosphere of chamber 22 through recirculation conduit 32. A dryer 46 is disposed within recirculation conduit 32 between blower 42 and second end 36. Dryer 46 is configured to remove moisture from the atmosphere of chamber 22 passing through recirculation conduit 32 as is conventionally known. A first valve 38 is disposed in recirculation conduit 32 between first end 34 of recirculation conduit 32 and blower 42 of recirculation conduit 32. A second valve 48 is disposed in recirculation conduit 32 between dryer 46 and second end 36. First valve 38 and second valve 48 are each movable between open and closed positions.

A bellows system 58 (shown schematically in FIG. 1) is fluidly connected to chamber 22 for regulating pressure therein. Other suitable means for regulating pressure include, but are not limited to, a pressure control valve, a rupture disk, or other conventionally known device.

Pressure sensor 59 is located within chamber 22 to provide a signal indicative of the pressure therein. By way of example and not limitation, pressure sensor 59 can be a load-cell-based pressure sensor or other conventional pressure-sensing device.

A first heater 24 and an enclosed vessel 70 are disposed within chamber 22. Vessel 70 defines a cavity 72 having a fixed volume. A movable lid 74 is attached to vessel 70 for enclosing cavity 72. In the embodiment shown, lid 74 is pivotally connected to vessel 70, and is movable between an open position and a closed position in response to means for actuating lid 74, such as a motor (not shown). When lid 74 is in the open position, cavity 72 is in fluid communication with chamber 22. When lid 74 is in the closed position, vessel 70 is enclosed such that cavity 72 is fluidly isolated from chamber 22. It should be appreciated that lid 74 may be connected with vessel 70 by alternative means, such as means for sliding lid 74 between the open and closed positions. It should be further appreciated that lid 74 may be replaced by other isolation means, such as one or more valves, that has one position for isolating cavity 72 from chamber 22 and another position for fluidly connecting cavity 72 and chamber 22. A second heater 88 is disposed within cavity 72.

In an alternative embodiment, vessel 70 is disposed outside of chamber 22. In this alternative embodiment, a conduit is connected between vessel 70 and housing 20 such that cavity 72 is in fluid communication with chamber 22 when lid 74 is in the open position.

Enclosed vessel 70 has an input port 92 defined therein. A first conduit 102 fluidly connects input port 92 to a source 104 for storing an aqueous solution of hydrogen peroxide. For the purpose of illustrating the present invention, the aqueous solution of hydrogen peroxide is a solution of 35% hydrogen peroxide and 65% water by weight. A first supply valve 112 is disposed in first conduit 102. First supply valve 112 is movable to control the flow of the aqueous solution of hydrogen peroxide from source 104 to cavity 72.

A second conduit 114 is fluidly connected to first conduit 102 between input port 92 and first supply valve 112. Second conduit 114 fluidly connects first conduit 102 to a water supply 116. In one embodiment, water supply 116 provides a source of deionized (DI) water. A second supply valve 118 is disposed within second conduit 114. Second supply valve 112 is movable to control the flow of water from supply 116 to cavity 72.

It should be appreciated that by combining an aqueous solution of hydrogen peroxide having one concentration of hydrogen peroxide with various amounts of water, aqueous solutions of hydrogen peroxide of various other concentrations of hydrogen peroxide can be produced within cavity 72.

A drain outlet 82 is defined within a bottom portion of vessel 70. A drain line 84 is in fluid communication with drain outlet 82 to connect drain outlet 82 with a drain. Drain line 84 is fluidly connected to cavity 72 of vessel 70 and a drain valve 86 is disposed in drain line 84 to control fluid flow from cavity 72 through drain line 84.

A concentration sensor 122 is disposed within cavity 72 of vessel 70. Concentration sensor 122 is configured to generate a signal indicative of a concentration of liquid hydrogen peroxide in an aqueous solution. In the illustrated embodiment, concentration sensor 122 is an electrochemical sensor (e.g., a capacitive type sensor). A first temperature sensor 124 is also disposed in cavity 72. First temperature sensor 124 provides a signal indicative of the temperature of the aqueous solution of hydrogen peroxide inside cavity 72.

A humidity sensor 126 and a second temperature sensor 128 are disposed in chamber 22 of housing 20. Humidity sensor 126 provides a signal indicative of the humidity level within chamber 22, while second temperature sensor 128 provides a signal indicative of the temperature within chamber 22.

A sensor 132 is also disposed within chamber 22 of housing 20. Sensor 132 is the sensor to be calibrated in accordance with calibration apparatus 10 of the present invention. In particular, sensor 132 is a sensing device (i.e., an IR sensor, electrochemical sensor, or other type of sensor for sensing the concentration of vaporized hydrogen peroxide) configured to generate a signal that is indicative of a measured concentration of vaporized hydrogen peroxide within chamber 22.

It is also contemplated that multiple sensors to be calibrated can be disposed within chamber 22. In this regard, multiple sensors can be calibrated during the same calibration cycle in accordance with the present invention, as will be discussed further below.

A controller 150 is provided for controlling the operation of calibration apparatus 10. Controller 150 is electrically connected to concentration sensor 122, first temperature sensor 124, humidity sensor 126, second temperature sensor 128, sensor 132, first valve 38, second valve 48, motor 44, dryer 46, pressure sensor 59, first supply valve 112, second supply valve 118, means for actuating lid 74 (not shown), and drain valve 86. In the embodiment shown, controller 150 is also connected to an operator interface 152 for providing visual and/or audible information, and for receiving operating instructions.

Controller 150 is configured to receive the signal generated by sensor 132 that is indicative of the measured concentration of vaporized hydrogen peroxide within chamber 22. Controller 150 is also programmed to store predetermined data such as look-up tables and/or mathematical equations that correlate a concentration of liquid hydrogen peroxide at a predetermined temperature to a concentration of vaporized hydrogen peroxide at generally the same temperature. In the illustrated embodiment, the stored look-up tables are Tables 1 and 2, discussed further below. The stored mathematical equations are equations 1-11, discussed further below. Further, controller 150 may be configured to generate output signals to sensor 132 for modifying the signal generated by sensor 132 that is indicative of the measured concentration of vaporized hydrogen peroxide in chamber 22. In this regard, the signal generated by sensor 132 that is indicative of the measured concentration of vaporized hydrogen peroxide may be adjustable such that the measured concentration is equal to the actual concentration of vaporized hydrogen peroxide in chamber 22.

The present invention can be better understood from the following brief explanation of a multi-component, liquid-phase, vapor-phase system at phase equilibrium. As used herein, the term "phase equilibrium" indicates that the concentrations of the components of the liquid and vapor phases are generally constant and the two phases have the same temperature and pressure. For example, when a system is at phase equilibrium, the rate at which a particular component, e.g. hydrogen peroxide or water, leaves the liquid phase and enters the vapor phase equals the rate at which the component leaves the vapor phase and enters the liquid phase.

In a closed, multi-component, liquid-phase, vapor-phase system at equilibrium, the relative concentrations of the components of the phases can be determined because the concentrations, volume, pressure, and temperature are generally fixed, i.e., are at an essentially steady state such that they do not change.

In the present invention, hydrogen peroxide and water are components of a liquid-vapor system at equilibrium. The concentration of vaporized hydrogen peroxide, i.e. concentration of hydrogen peroxide in the vapor phase, is determined according to the following equations. In the following equations, a concentration of vaporized hydrogen peroxide is related to a concentration of hydrogen peroxide in an aqueous solution when the aqueous solution of hydrogen peroxide is in equilibrium with the vaporized hydrogen peroxide. Unless stated otherwise, the partial pressures, activity coefficients, and fractions used in the equations below refer to the aqueous solution of hydrogen peroxide. In connection with the present invention, the presence of nitrogen, oxygen, and other components of air within chamber 22 does not appreciably affect the applicability of the following equations.

Equations 1 through 7 shown below are used to determine the mole fraction of vaporized hydrogen peroxide for a particular temperature and for a particular mole fraction of liquid hydrogen peroxide. In this regard, the mole fraction of hydrogen peroxide gas over a hydrogen peroxide-water solution (i.e., the aqueous solution of hydrogen peroxide) is given by equation 1.

$$y_h = \frac{p_{hg} x_h \gamma_h}{P} = \frac{p_{hg} x_h \gamma_h}{(p_{wg} x_w \gamma_w) + (p_{hg} x_h \gamma_h)} \quad 1)$$

Where:
$y_h$=mole fraction of hydrogen peroxide in the vapor phase, i.e. the final concentration,
$p_{hg}$=vapor pressure of hydrogen peroxide (mm Hg) (see equation 7 below),
$x_h$=mole fraction of hydrogen peroxide in liquid form,
$\gamma_h$=activity coefficient for hydrogen peroxide,
P=total vapor pressure (mm Hg) (see equation 2 below),
$P_{wg}$=vapor pressure of water (mm Hg) (see equation 6 below),
$x_w$=mole fraction of water, and
$\gamma_w$=activity coefficient for water.

The total vapor pressure of the aqueous solution of hydrogen peroxide is given in equation 2 below.

$$P = p_{wg} x_w \gamma_w + p_{hg} (1-x_w) \gamma_h \quad 2)$$

The activity coefficient for water is given in equation 3 below.

$$\gamma_w = \exp\left(\frac{(1-x_h)^2}{RT}[B_o + B_1(1-4x_w) + B_2(1-2x_w)(1-6x_w)]\right) \quad 3)$$

$x_h$=mole fraction of hydrogen peroxide,
R=1.987 cal/gmole-K ideal gas constant,
$B_0$=coefficient for calculation of activity coefficient=−1017+0.97*T,
$B_1$=coefficient for calculation of activity coefficient=85,
$B_2$=coefficient for calculation of activity coefficient=13, and
T=water vapor temperature (K).

The activity coefficient for hydrogen peroxide can be determined using equation 4 below.

$$\gamma_h = \exp\left(\frac{(x_w)^2}{RT}[B_o + B_1(3-4x_w) + B_2(1-2x_w)(5-6x_w)]\right) \quad 4)$$

The mole fraction of hydrogen peroxide can be calculated using equations 5a and 5b below.

$$x_h = (P_0 * M_w)/(M_h * (100 - P_0) + P_0 * M_w) \quad 5a)$$

$$x_h = \frac{WM_w}{M_h(100-W) + WM_w} \quad 5b)$$

Where:
$x_h$=mole fraction of hydrogen peroxide $x_h$=1−$X_w$,
$P_O$=percent hydrogen peroxide in gas or liquid form (mass fraction),
$M_w$=molecular weight of water=18.016 grams/mole,
$M_h$=molecular weight of hydrogen peroxide=34.016 grams/mole, and
W=weight % of hydrogen peroxide (mass fraction).

For temperatures above 32° F., the vapor pressure of water can be calculated using equation 6 as follows:

$$P_{wg}=\text{Exp}(C_8/(TF+460)+C_9+C_{10}*(TF+460)+C_{11}*(TF+460)^2+C_{12}*(TF+460)^3+C_{13}*\text{Log}(TF+460)) \quad 6)$$

Where:
$P_{wg}$=vapor pressure of water at saturation (psi),
TF=vapor temperature (° F.),
$C_8$=−1 0440.397,
$C_9$=−11.29465,
$C_{10}$=−0.027022,355,
$C_{11}$=0.00001289036,
$C_{12}$=−2.4780681E-09, and
$C_{13}$=6.5459673.

The vapor pressure of anhydrous hydrogen peroxide can be calculated as shown in equation 7 below.

$$p_{hg} = 10^{\left(44.5760-\frac{4025.3}{T}-12.996 logT+0.0046055T\right)} \quad 7)$$

Where:
T=vapor temperature (K).

In the present invention, equations 1 through 7 above can be used to develop Table 1, shown below. It should be appreciated that Table 1 could be further expanded using equations 1 through 7.

Table 1 provides the mass fraction of hydrogen peroxide in vapor form at a given mass fraction of hydrogen peroxide in liquid form for various temperatures expressed as a mass fraction.

n=number of moles,
R=universal Gas Constant (0.082 liter-atm/mole-K), and
T temperature of vapor (K).

The concentration of peroxide or water vapor is usually given in mass per unit volume. Equation 8 can be arranged to calculate concentration as shown in equation 9 below.

$$C = w/V = Mn/V = MxP/(RT)*(1000 \text{ mg/g})\left(\frac{1 \text{ atm}}{760 \text{ mmHg}}\right) \quad 9)$$

Where:

C = concentration of vapor(mg/liter), w = mass (mg),

V = volume (liter),

M = molecular weight of water or hydrogen peroxide
    (grams/mole),
  = 34.016 grams/mole for peroxide,
  = 18.016 grams/mole for water, x = vapor mole fraction, P = total vapor pressure of aqueous solution of hydrogen peroxide (i.e., the water and hydrogen peroxide mix) (mm Hg), R = universal Gas Constant (0.082 liter-atm/mole-K), T = temperature of vapor (K), and n = number of moles.

Knowing the mass fraction of liquid hydrogen peroxide at a given temperature, equation 5 is used to convert the mass fraction of liquid hydrogen peroxide to mole fraction; equations 3 and 4 are to determine $\gamma_w$ and $\gamma_h$; equation 2 is used to determine P (total vapor pressure of the aqueous solution of

TABLE 1

| Temp | | Liquid State Hydrogen Peroxide Concentration | | | | | | | | |
|---|---|---|---|---|---|---|---|---|---|---|
| | | 17.34% | 32.07% | 44.73% | 55.73% | 65.38% | 73.90% | 81.50% | 88.31% | 94.44% |
| ° F. | ° C. | Mass fraction of hydrogen peroxide in a vapor state as a function of temperature and concentration of hydrogen peroxide in an aqueous solution of hydrogen peroxide. | | | | | | | | |
| 50 | 10 | 0.56% | 1.50% | 3.35% | 6.76% | 12.44% | 21.70% | 35.28% | 53.75% | 75.96% |
| 68 | 20 | 0.56% | 1.69% | 3.71% | 7.47% | 13.61% | 23.21% | 37.10% | 55.42% | 77.05% |
| 77 | 25 | 0.56% | 1.87% | 4.07% | 8.00% | 14.27% | 24.11% | 38.25% | 56.44% | 77.66% |
| 86 | 30 | 0.56% | 1.87% | 4.26% | 8.34% | 14.92% | 25.14% | 39.26% | 57.46% | 78.26% |
| 104 | 40 | 0.75% | 2.24% | 4.80% | 9.38% | 16.38% | 26.88% | 41.36% | 59.24% | 79.38% |

The ideal gas law can be used to estimate the saturation concentration level of the hydrogen peroxide and water vapor components at a given temperature, as shown in Table 2 below. The ideal gas law is given in equation 8 below:

$$PV=nRT \quad 8)$$

Where:
P=total vapor pressure (mm Hg),
V=volume (liters), hydrogen peroxide); equations 6 and 7 are used to determine vapor pressure $P_{wg}$ and $P_{hg}$; equation 1 is used to calculate $y_h$; and equation 9 is used to determine the saturation concentration level in mg/liter.

Table 2 provides the saturation concentration in milligrams per liter of vapor phase hydrogen peroxide as a function of temperature and the concentration of liquid hydrogen peroxide in an aqueous solution expressed as a mass fraction.

TABLE 2

| | | Liquid State Hydrogen Peroxide Concentration | | | | | | | | |
|---|---|---|---|---|---|---|---|---|---|---|
| | | 17.34% | 32.07% | 44.73% | 55.73% | 65.38% | 73.90% | 81.50% | 88.31% | 94.44% |
| Temp | | Saturation Concentration Level (mg/liter) of vapor phase hydrogen | | | | | | | | |
| ° F. | ° C. | peroxide as a function of temperature and liquid state concentration | | | | | | | | |
| 50 | 10 | 0.05 | 0.11 | 0.20 | 0.32 | 0.46 | 0.62 | 0.78 | 0.94 | 1.08 |
| 68 | 20 | 0.09 | 0.23 | 0.41 | 0.67 | 0.96 | 1.29 | 1.63 | 1.96 | 2.47 |
| 77 | 25 | 0.12 | 0.33 | 0.60 | 0.96 | 1.37 | 1.83 | 2.31 | 2.77 | 3.19 |
| 86 | 30 | 0.16 | 0.44 | 0.84 | 1.34 | 1.92 | 2.57 | 3.22 | 3.87 | 4.46 |
| 104 | 40 | 0.35 | 0.89 | 0.92 | 2.57 | 3.65 | 4.84 | 6.07 | 7.26 | 8.36 |

The atmosphere within the calibration chamber is air at or near atmospheric pressure. The presence of nitrogen, oxygen, and other components of air in the calibration apparatus does not appreciably affect the values of Tables 1 and 2.

It is believed that the presence of water in the calibration chamber may result in some change to the mass fraction of the hydrogen peroxide. While only a small change may occur, it is desirable to remove water from the calibration chamber before the liquid hydrogen peroxide is introduced therein.

The present invention will now be discussed with respect to the operation of calibration apparatus 10. In one embodiment, calibration apparatus 10 operates according to a calibration cycle. A calibration cycle includes a drying step, a filling step, an equilibration step, and a calibration step. The drying step and the filling step are independent of each other. After the drying step and the filling step are both complete, the equilibration step is performed. After the equilibration step is complete, the calibration step is performed.

If a pressure within chamber 22 increases beyond a predetermined maximum pressure level during any step of a calibration cycle, bellows system 58 acts to relieve the pressure within chamber 22. It should be appreciated that bellows system 58 could act to control pressure within chamber 22 at a predetermined pressure.

It is recognized that hydrogen peroxide will decompose into water and oxygen throughout the calibration cycle. However, it has been observed that this decomposition does not change the "mass fraction" of the hydrogen peroxide within the accuracy of measurement. In this regard, it is believed that the decomposition of hydrogen peroxide will not significantly affect the relative proportions of water and hydrogen peroxide within chamber 22 during the calibration cycle.

Prior to a calibration cycle, first valve 38, second valve 48, drain valve 86, first supply valve 112, and second supply valve 118 are all in their respective closed positions. Lid 74 is in its closed position, and motor 44 is inactive. Also prior to a calibration cycle, sensor 132, the sensor to be calibrated, is placed within chamber 122 and electrically connected to controller 150. It is contemplated that multiple sensors to be calibrated can be placed within chamber 22 and electrically connected to controller 150. All of the sensors to be calibrated could then be calibrated in one calibration cycle.

In one embodiment, chamber 22 is assumed to contain an atmosphere of air at or near atmospheric pressure before the calibration cycle begins. As indicated above, the calibration cycle begins with the drying step. The purpose of the drying step is to remove moisture present within the atmosphere of chamber 22 prior to a calibration cycle. Controller 150 initiates the drying step by actuating first valve 38 and second valve 48 such that they are in their respective open positions. Controller 150 then actuates motor 44 and dryer 46 such that the atmosphere of chamber 22 of housing 20 flows through recirculation conduit 32. As the atmosphere of chamber 22 flows through recirculation conduit 32, it passes through dryer 46 and moisture is removed therefrom. The drying step continues until the humidity level inside chamber 22, as indicated by humidity sensor 126, is reduced to a predetermined level that is so low that it does not appreciably affect the mass fraction of the hydrogen peroxide. The predetermined humidity level that will not affect the mass fraction of hydrogen peroxide will depend upon the volume of chamber 22, water content and volume of the sterilant. Preferably, the predetermined humidity level is at or near zero percent. When humidity sensor 126 indicates that the humidity level in chamber 22 has been reduced to the predetermined humidity level, controller 150 deactivates dryer 46 and motor 44 and moves first valve 38 and second valve 48 to their closed positions. At this point in the calibration cycle, recirculation conduit 32, blower 42, and dryer 46 are isolated from chamber 22 and the drying step is complete.

In one embodiment, the filling step begins immediately after the drying step is complete. Controller 150 initiates the filling step by actuating first supply valve 112 to introduce the aqueous solution of hydrogen peroxide from source 104 into cavity 72. Controller 150 actuates second supply valve 118 to introduce water into cavity 72. By actuating valves 112 and 118 in varying amounts, controller 150 can introduce an aqueous solution of hydrogen peroxide having a predetermined concentration of hydrogen peroxide into cavity 72. Preferably, the predetermined concentration of hydrogen peroxide in the aqueous solution within cavity 72 is generally equal to a value of concentration of hydrogen peroxide in the aqueous solution provided in Table 1 or Table 2.

The concentration of hydrogen peroxide in the aqueous solution within cavity 72 can be chosen such that the resulting concentration of vaporized hydrogen peroxide is near the concentration that sensor 132 (i.e., the sensor to be calibrated) is to be exposed to during a decontamination cycle. For example, in one embodiment sensor 132 is to be used during decontamination of rooms. The concentration of vaporized hydrogen peroxide used during the decontamination of rooms is generally in the range of about 0.35 to 0.56 mg/liter. Therefore, for such a sensor 132, the concentration of hydrogen peroxide in the aqueous solution within cavity 72 is chosen to provide a concentration of vaporized hydrogen peroxide in chamber 22 within the range of about 0.35 to 0.56 mg/liter.

The equilibration step is initiated after both the drying step and the filling step have been completed. Chamber 22 and cavity 72 are maintained at a predetermined temperature during the equilibration and calibration steps. To this end, controller 150 operates first heater 24 and second heater 88 such that chamber 22 and cavity 72 are maintained at a predetermined temperature.

Controller 150 initiates the equilibration step by moving lid 74 to its open position such that cavity 72 is fluidly connected to chamber 22. When lid 74 is open, the components of the aqueous solution of hydrogen peroxide within cavity 72 enter the vapor phase at a first rate, i.e., a rate of evaporation. In other words, hydrogen peroxide and water begin to evaporate and enter the vapor phase. It is appreciated that in a liquid-vapor system, evaporation and condensation occur simultaneously at the gas/liquid interface. Consequently, once hydrogen peroxide and water are present in a vapor phase, they begin to enter the liquid phase by condensing at a second rate, i.e., rate of condensation. As the liquid and vapor phases approach equilibrium, the rate of evaporation and the rate of condensation approach each other. When the liquid and vapor phases are in equilibrium, the evaporation rate and the condensation rate are generally equal. The equilibration step continues until phase equilibrium has been reached. When phase equilibrium has been reached, the equilibration step is complete and the calibration step can begin.

In one embodiment, controller 150 is programmed to determine that phase equilibrium has been reached in chamber 22 by monitoring signals generated by humidity sensor 126 and sensor 132, the sensor to be calibrated. In this regard, controller 150 determines that phase equilibrium has been reached when the signals generated by humidity sensor 126 and sensor 132 are generally stable.

Alternatively, controller 150 is programmed to determine when a predetermined time period has elapsed after lid 74 has been removed. The predetermined time period is chosen such that the liquid phase and the vapor phase within chamber 22 have reached equilibrium when the predetermined time period elapses. Bellows system 58 maintains the pressure in chamber 22 substantially at atmospheric pressure.

In one embodiment, the calibration step is initiated immediately following the completion of the equilibration step, i.e., after phase equilibrium has been reached. For clarity, the discussion below regarding the use of the tables will refer to Table 1. However, it should be understood that either Table 1 or Table 2 can be used in connection with the present invention.

During the calibration step, controller 150 determines both the actual concentration of vaporized hydrogen peroxide within chamber 22 and the measured concentration of vaporized hydrogen peroxide within chamber 22, as indicated by the signal generated by sensor 132.

In one embodiment of the present invention, controller 150 determines the actual concentration of vaporized hydrogen peroxide in chamber 22 directly using equations 1-9, as discussed in detail above.

Controller 150 determines the measured concentration of vaporized hydrogen peroxide within chamber 22 in accordance with the signal generated by sensor 132. Controller 150 then compares the measured concentration to the determined actual concentration of vaporized hydrogen peroxide within chamber 22 in order to obtain an error value indicative of the difference between the measured and actual concentration. The error value is used to "calibrate" sensor 132. In this respect, sensor 132 may be calibrated by applying a "correction factor" to the concentration value indicated by sensor 132. Alternatively, sensor 132 may be calibrated by directly modifying the internal programming of sensor 132 so that the concentration value indicated by sensor 132 is substantially equal to the actual concentration of vaporized hydrogen peroxide. Modification to the internal programming of sensor 132 may be done manually, or through the use of a programming device or system, including controller 150.

In the case of an electrochemical sensor, a (millivolt) signal is generated by the sensor that is proportional to the concentration of vaporized hydrogen peroxide. The generated signal is typically in the range of about 4-22 milliamps. A slope and intercept value may be determined by obtaining two (2) milliamp values for two (2) corresponding vaporized hydrogen peroxide concentrations. Other types of sensors, such as near IR sensors, produce results in units of mg/l or ppm.

Controller 150 can be programmed to confirm the actual concentration of vaporized hydrogen peroxide within chamber 22 by utilizing humidity sensor 126. In this regard, controller 150 determines the measured humidity within chamber 22 in accordance with the humidity signal generated by humidity sensor 126. Next, controller 150 determines a humidity value within chamber 22 that corresponds to the actual concentration of vaporized hydrogen peroxide determined as described above. In this regard, controller 150 subtracts the concentration of the actual value of vaporized hydrogen peroxide within chamber 22 from 100 to determine the theoretical humidity value. Controller 150 then compares the measured humidity value to the theoretical humidity value. If the measured humidity value is generally equal to the theoretical humidity value, then the actual concentration of vaporized hydrogen peroxide in chamber 22 as determined above is confirmed.

In another embodiment of the present invention, the concentration of vaporized hydrogen peroxide within chamber 22 during the calibration phase can be easily varied from one calibration cycle to another. In this regard, the concentration of hydrogen peroxide within the aqueous solution of hydrogen peroxide within cavity 72 can be chosen such that sensor 132 to be calibrated is exposed to a range of vaporized hydrogen peroxide concentrations during successive calibration cycles. For example, water from water supply 116 is introduced into cavity 72 during the filling step of an initial calibration cycle. A concentrated aqueous solution of hydrogen peroxide is introduced from source 104 into cavity 72 to create a dilute initial aqueous solution of hydrogen peroxide within cavity 72. The initial calibration cycle is then completed. In subsequent calibration cycles, concentrated aqueous hydrogen peroxide is introduced from source 104 into the aqueous solution of hydrogen peroxide already within cavity 72 to form successively more concentrated aqueous solutions of hydrogen peroxide within cavity 72. In each of these subsequent calibration cycles, sensor 132 is exposed to successively higher concentrations of vaporized hydrogen peroxide during the calibration step.

A calibration apparatus according to an alternative embodiment of the present invention will now be described with reference to FIG. 2. Calibration apparatus 210 generally comprises an enclosure 220, a recirculation conduit 222, an open vessel 250 located within enclosure 220, a reservoir 260 and a densitometer 280. Calibration apparatus 210 operates at atmospheric temperature.

Enclosure 220 includes an output port 220a and an input port 220b that are fluidly connected with opposite ends of recirculation conduit 222. In the illustrated embodiment, a catalytic converter 240, a blower 242 and a dryer 244 are disposed in recirculation conduit 222. A catalytic converter 240 is located downstream of output port 220a, while dryer 244 is located upstream of input port 220b. Catalytic converter 240 is operable to destroy hydrogen peroxide flowing therethrough, by conventionally known means. Dryer 244 is operable to remove moisture, by conventionally known means. Blower 242 is disposed in recirculation conduit 222 between catalytic converter 240 and dryer 244. In the illustrated embodiment, blower 242 includes a "ring compressor"

to stop fluid flow therethrough when blower 242 is deactivated. A temperature sensor 246 and a humidity sensor 248 are also disposed in recirculation conduit 222. In the illustrated embodiment, temperature sensor 246 and humidity sensor 248 are downstream of catalytic converter 240, between catalytic converter 240 and blower 242. Humidity sensor 248 provides a signal indicative of relative humidity.

A temperature sensor 224 is located within enclosure 220 to provide a signal indicative of the temperature therein.

Open vessel 250, located within enclosure 220, is fluidly connected with reservoir 260 by a first fluid conduit 252. Reservoir 260 contains an aqueous solution of hydrogen peroxide, i.e., the liquid sterilant. In the illustrated embodiment, reservoir 260 takes the form of a conventional bottle. A first reversible pump 254 is disposed within first fluid conduit 252 to transfer the liquid sterilant between reservoir 260 and open vessel 250. A float switch 256 is located within open vessel 250 to indicate when a known fluid level has been reached within open vessel 250.

The density of the liquid sterilant in reservoir 260 is determined using densitometer 280, as will be described in detail below. Densitometer 280 is comprised of a tube 282, a pressure transducer 284, a float switch 286 and a temperature sensor 288. Pressure transducer 284 is located at the lower end of tube 282. Float switch 286 is used to indicate when a known fluid height (h) has been reached within tube 282. A second fluid conduit 272 connects densitometer 280 with first fluid conduit 252. A second reversible pump 274 is disposed in second fluid conduit 272 to transfer liquid sterilant between reservoir 260 and densitometer 280. As will be described in further detail below, the density of the liquid sterilant is determined using the pressure indicated by pressure transducer 284, and the known fluid height (h) within tube 282. The concentration of liquid hydrogen peroxide in the liquid sterilant is determined from the fluid temperature in tube 282 (indicated by temperature sensor 288), the calculated density of the liquid sterilant, and known equations.

A controller 290 is programmed to control operation of calibration apparatus 210 in the manner discussed in detail below. Controller 290 provides control signals to activate and deactivate blower 242, dryer 244, and reversible pumps 254, 274. Controller 290 receives signals from temperature sensor 224, temperature sensor 246, humidity sensor 248, float switch 256, pressure transducer 284, float switch 286 and temperature sensor 288. It should be appreciated that controller 290 may take the form of a microcontroller or microprocessor.

Figure 2:
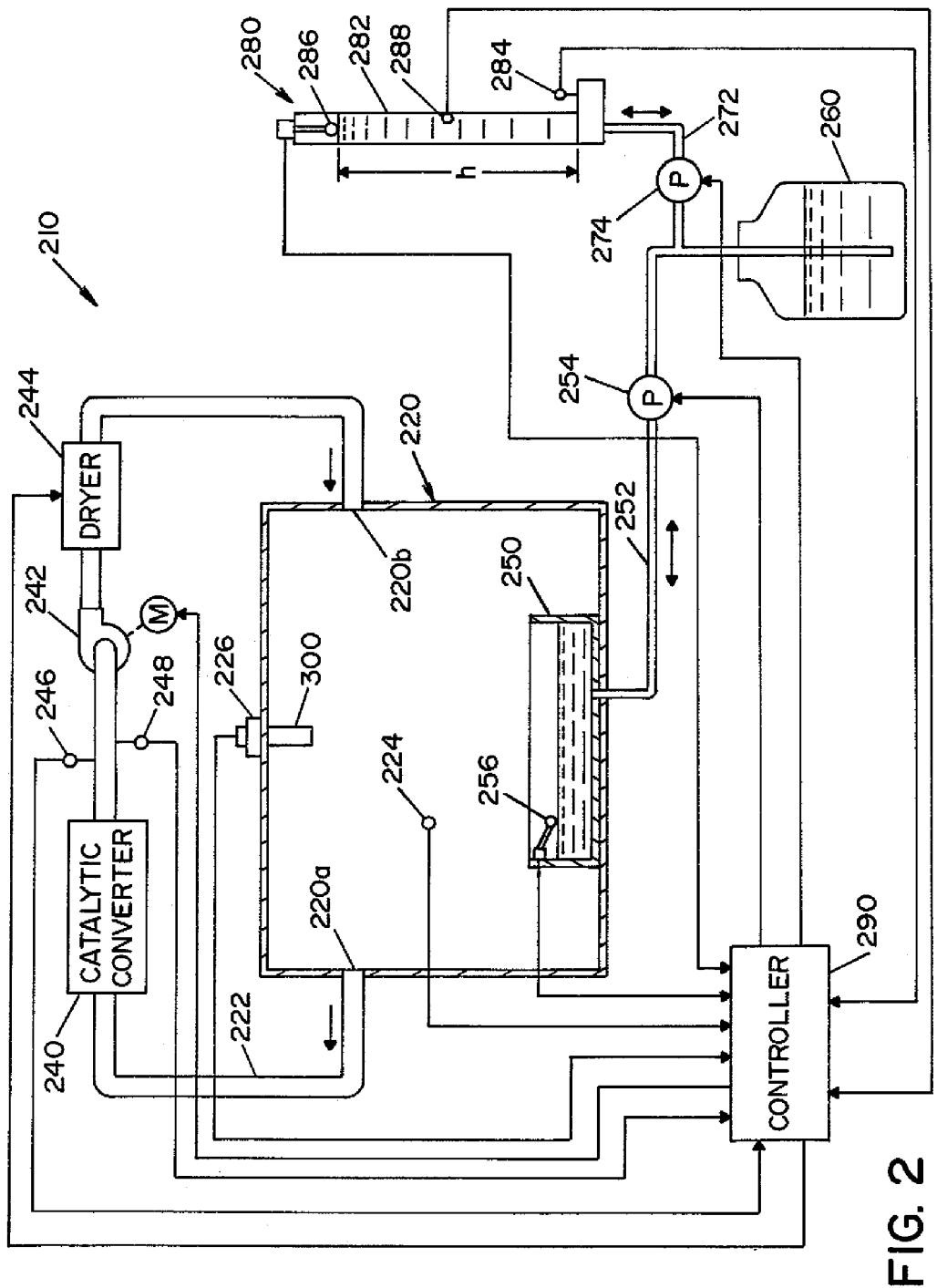
FIG. 2 is a schematic view of an alternative embodiment of an apparatus for calibrating a sensor used to sense the concentration of vaporized hydrogen peroxide.

The concentration sensor (i.e., concentration sensor 300) that is being calibrated by calibration apparatus 210 is located within enclosure 220, as indicated in FIG. 2. Concentration sensor 300 provides a signal to controller 290 that is indicative of vaporized hydrogen peroxide concentration inside enclosure 220. In the illustrated embodiment concentration sensor 300 is located in a holder 226. It should be appreciated that holder 226 may be configured to hold more than one concentration sensor 300, thereby allowing simultaneous calibration of multiple concentration sensors.

Operation of calibration apparatus 210 will now be described in detail. First, blower 242 is activated until a predetermined absolute humidity level (e.g., 0.5 mg/liter) is reached inside enclosure 220. Absolute humidity within enclosure 220 is monitored by controller 290 using the relative humidity indicated by humidity sensor 248 and the temperature indicated by temperature sensor 246.

Next, pump 274 is activated by controller 290 to transfer liquid sterilant from reservoir 260 to densitometer 280. In this regard, pump 274 is activated until the fluid level within tube 282 has reached a predetermined level (i.e., height h), as indicated by activation of float switch 286. Pressure transducer 284 provides a signal to controller 290 indicative of the pressure level within tube 282, and temperature sensor 288 provides a signal to controller 290 indicative of the temperature of the liquid sterilant within tube 282. Accordingly, controller 290 determines the density of the liquid sterilant within tube 282 using the following equation from hydrostatics:

$$P = \rho \cdot h \quad (1A)$$

Where:
P=pressure level in tube 282 (as determined from pressure transducer 284),
ρ=density, and
h=fluid height (known).
Equation (1A) can be solved for density, giving:

$$\rho = P/h \quad (2A)$$

After the density ρ is determined by equation (2A), the following equation can be used to determine the concentration of liquid hydrogen peroxide in the liquid sterilant:

$$\rho = a + b \cdot \omega + c \cdot \omega^2 + d \cdot \omega^3 \quad (3A)$$

Where:
a, b, c and d are coefficients determined as a function of temperature from the table below, and
ω=concentration of liquid hydrogen peroxide in the liquid sterilant, in comparison to water, by mass (35%=0.35).

TABLE 3

| Temperature (° C.) | a | b | c | d |
|---|---|---|---|---|
| 0 | 0.9998 | 0.39939 | 0.01758 | 0.05470 |
| 10 | 0.9997 | 0.36790 | 0.06208 | 0.02954 |
| 25 | 0.9970 | 0.34672 | 0.06995 | 0.02885 |
| 50 | 0.9880 | 0.31382 | 0.09402 | 0.01910 |
| 96 | 0.9612 | 0.27652 | 0.11956 | — |

Interpolation can be used to determine coefficients at temperatures other than those identified in the above Table 3.

It will be appreciated that alternative techniques may be used to determine density of the liquid sterilant.

With the temperature and density of the liquid hydrogen peroxide known, equation (3A) can be used to determine the liquid concentration of hydrogen peroxide by trial and error. Alternative, a solver routine can be used. The liquid concentration of hydrogen peroxide may also be determined using other means such as a chemical assay.

After temperature and density values have be determined using densitometer 280, controller 290 activates pump 274, in reverse, to return the liquid sterilant in tube 282 to reservoir 260. Thereafter, controller 290 activates pump 254 to transfer liquid sterilant from reservoir 260 to open vessel 250 located inside enclosure 220. In this regard, pump 254 remains activated until float switch 256 is activated, thereby indicating to controller 290 that a predetermined fluid level has been reached in open vessel 250.

Liquid hydrogen peroxide in open vessel 250 is then allowed to diffuse into enclosure 220. Controller 290 monitors the concentration (indicated by concentration sensor 300) versus time, and allows the signal from concentration sensor 300 to stabilize, thereby indicating a phase equilibrium. Thereafter, the liquid concentration of hydrogen peroxide, as determined above, is used along with equations 1-9 (described in detail above in connection with the first embodiment of the present invention) to determine the actual concentration of vaporized hydrogen peroxide in enclosure 220.

Controller 290 determines the measured concentration of vaporized hydrogen peroxide within enclosure 220 in accordance with the signal generated by concentration sensor 300. The measured concentration of vaporized hydrogen peroxide is compared to the actual concentration of vaporized hydrogen peroxide, as determined using equations 1-9. Concentration sensor 300 is then calibrated in the same manner as described above in connection with sensor 132.

After calibration of concentration sensor 300 has been completed, controller 290 activates pump 254, in reverse, to return the liquid sterilant from open vessel 250 to reservoir 260. Once the liquid sterilant has been completely drained from open vessel 250, controller 290 activates blower 242 for a time sufficient to deplete (i.e., aerate) all vaporized hydrogen peroxide inside enclosure 220. Following aeration, controller 290 indicates to the user that it is safe to remove concentration sensor 300 from holder 226.

The foregoing descriptions are specific embodiments of the present invention. It should be appreciated that these embodiments are described for purposes of illustration only, and that those skilled in the art may practice numerous alterations and modifications without departing from the spirit and scope of the invention. It is intended that all such modifications and alterations be included insofar as they come within the scope of the invention as claimed or the equivalents thereof.

Having described the invention, the following is claimed:

1. An apparatus for calibrating a concentration sensor for sensing concentration of vaporized hydrogen peroxide, said apparatus comprising:
   an enclosure defining a chamber;
   a first temperature sensor for generating a first signal indicative of the temperature within the chamber;
   a vessel defining a cavity, said vessel including isolation means movable between a closed position for isolating the cavity from the chamber and an open position wherein the cavity is in fluid communication with the chamber;
   first supply means for supplying an aqueous solution of liquid hydrogen peroxide to the cavity;
   a first concentration sensor for generating a second signal indicative of a concentration of liquid hydrogen peroxide within the cavity;
   a controller storing data for correlating a concentration of liquid hydrogen peroxide at a predetermined temperature to a concentration of vaporized hydrogen peroxide, said vaporized hydrogen peroxide being derived from said aqueous solution of liquid hydrogen peroxide, wherein said controller includes:
      means for receiving the first signal generated by the first temperature sensor indicative of the temperature within the chamber and the second signal generated by the first concentration sensor indicative of the concentration of liquid hydrogen peroxide within the cavity;
      means for moving said isolation means from the closed position to the open position, thereby releasing vaporized hydrogen peroxide into said chamber;
      means for receiving a third signal generated by a second concentration sensor located within said chamber, said third signal indicative of a measured vaporized hydrogen peroxide concentration inside said chamber;
      means for determining an actual concentration of vaporized hydrogen peroxide inside said chamber using said first signal, said second signal and said stored data;
      means for comparing said measured concentration to said actual concentration to determine an error value; and
      means for calibrating said second concentration sensor in accordance with the determined error value.

2. An apparatus for calibrating a concentration sensor according to claim 1, wherein the apparatus further includes:
   first heating means for heating liquid hydrogen peroxide within said cavity; and
   second heating means for heating vaporized hydrogen peroxide within said chamber.

3. An apparatus for calibrating a concentration sensor according to claim 1, wherein said vessel is disposed within said chamber.

4. An apparatus for calibrating a concentration sensor according to claim 3, wherein said isolation means is a movable lid.

5. An apparatus for calibrating a concentration sensor according to claim 1, wherein said isolation means includes a valve.

6. An apparatus for calibrating a concentration sensor according to claim 1, further comprising:
   means for removing moisture from said chamber.

7. An apparatus for calibrating a concentration sensor according to claim 1, wherein said means for calibrating determines a calibration factor to be applied to the measured vaporized hydrogen peroxide concentration indicated by said second concentration sensor.

8. An apparatus for calibrating a concentration sensor according to claim 1, wherein said means for calibrating modifies internal programming of said second concentration sensor such that the measured vaporized hydrogen peroxide concentration is substantially equal to the actual vaporized hydrogen peroxide concentration.

9. A method for calibrating a concentration sensor for sensing concentration of vaporized hydrogen peroxide, said method comprising the steps of:
   filling a cavity defined by an enclosed vessel with an aqueous solution of liquid hydrogen peroxide, said cavity isolated by isolation means from a chamber defined by an enclosure;
   storing data in a controller, said data correlating a concentration of liquid hydrogen peroxide at a predetermined temperature to a concentration of vaporized hydrogen peroxide;
   locating a concentration sensor to be calibrated within said chamber, said concentration sensor generating a signal indicative of a measured concentration of vaporized hydrogen peroxide within said chamber;
   moving said isolation means to put said cavity in fluid communication with said chamber, thereby releasing vaporized hydrogen peroxide into said chamber;
   determining a concentration of the liquid hydrogen peroxide within said cavity;
   determining a temperature within said cavity;
   determining an actual concentration of vaporized hydrogen peroxide inside said chamber using said stored data, the temperature within said cavity, and the concentration of liquid hydrogen peroxide within said cavity;
   comparing the measured concentration to the actual concentration to determine an error value; and
   calibrating said concentration sensor located within said chamber in accordance with the determined error value.

10. A method for calibrating a concentration sensor according to claim 9, further comprising the step of:
    removing moisture from said chamber prior to said step of moving said isolation means.

11. A method for calibrating a concentration sensor according to claim 9, wherein said calibrating step includes determining a calibration factor to be applied to the measured vaporized hydrogen peroxide concentration indicated by said concentration sensor.

12. A method for calibrating a concentration sensor according to claim 9, wherein said calibrating step includes modifying internal programming of said concentration sensor such that the measured vaporized hydrogen peroxide concentration is substantially equal to the actual vaporized hydrogen peroxide concentration.

13. A method for calibrating a concentration sensor according to claim 9, wherein said method further comprises a step of confirming said actual concentration of vaporized hydrogen peroxide inside said chamber.

14. A method for calibrating a concentration sensor according to claim 13, wherein the step of confirming said actual concentration of vaporized hydrogen peroxide includes the steps of:

determining a measured moisture humidity value within said chamber;

determining a theoretical humidity value within said chamber in accordance with said actual concentration of vaporized hydrogen peroxide;

comparing said theoretical humidity value to said measured humidity value, wherein if said theoretical humidity value is generally equal to said measured humidity value, said actual concentration of vaporized hydrogen peroxide is confirmed.

15. A method for calibrating a concentration sensor according to claim 9, said method further comprising the step of allowing a liquid phase of chemical components disposed within said chamber and a vapor phase of said chemical components disposed within said chamber to obtain equilibrium, wherein said chemical components include hydrogen peroxide and water.

16. A method for calibrating a concentration sensor according to claim 9, wherein said vessel is disposed within said chamber.

* * * * *